(12) United States Patent
Karato et al.

(10) Patent No.: US 9,244,016 B2
(45) Date of Patent: Jan. 26, 2016

(54) PEROXIDE INDICATOR

(71) Applicant: NiGK CORPORATION, Kawagoe-shi, Saitama (JP)

(72) Inventors: Ryo Karato, Kawagoe (JP); Nobuyuki Ando, Kawagoe (JP)

(73) Assignee: NiGK CORPORATION, Kawagoe-shi, Saitama (JP)

( * ) Notice: Subject to any disclaimer, the term of this patent is extended or adjusted under 35 U.S.C. 154(b) by 0 days.

(21) Appl. No.: 14/380,853

(22) PCT Filed: Feb. 27, 2013

(86) PCT No.: PCT/JP2013/055122
§ 371 (c)(1),
(2) Date: Aug. 25, 2014

(87) PCT Pub. No.: WO2013/129473
PCT Pub. Date: Sep. 6, 2013

(65) Prior Publication Data
US 2015/0050745 A1    Feb. 19, 2015

(30) Foreign Application Priority Data
Feb. 29, 2012 (JP) ................ 2012-043794

(51) Int. Cl.
| | | |
|---|---|---|
| G01N 21/78 | (2006.01) | |
| G01N 21/75 | (2006.01) | |
| G01N 31/22 | (2006.01) | |
| C01G 29/00 | (2006.01) | |
| C01G 30/00 | (2006.01) | |
| C01G 41/00 | (2006.01) | |

(52) U.S. Cl.
CPC ............. *G01N 21/78* (2013.01); *C01G 29/00* (2013.01); *G01N 31/226* (2013.01); *C01G 30/00* (2013.01); *C01G 41/00* (2013.01); *C01P 2004/90* (2013.01); *Y10T 428/2982* (2015.01); *Y10T 436/12* (2015.01); *Y10T 436/15* (2015.01); *Y10T 436/20* (2015.01); *Y10T 436/206664* (2015.01)

(58) Field of Classification Search
CPC ....... G01N 21/78; G01N 21/77; G01N 21/75; G01N 21/00; G01N 31/228; G01N 31/22; Y10T 436/00; Y10T 436/12; Y10T 436/15; Y10T 436/20; Y10T 436/206664; C01G 29/00; C01G 30/00; C01G 41/00; C01P 2004/90; C01P 2004/00
USPC ........ 436/135, 127; 422/50, 51; 428/402, 357
See application file for complete search history.

(56) References Cited

U.S. PATENT DOCUMENTS

| | | | |
|---|---|---|---|
| 5,702,955 A | 12/1997 | Pugia | |
| 6,485,978 B1 * | 11/2002 | Kirckof et al. ................... | 436/1 |
| 6,884,394 B1 | 4/2005 | Hehenberger et al. | |
| 8,343,768 B2 | 1/2013 | Kyung-Hee Song et al. | |
| 2003/0194346 A1 * | 10/2003 | Read .............................. | 422/28 |
| 2008/0267811 A1 | 10/2008 | Yamaguchi et al. | |
| 2010/0119410 A1 | 5/2010 | Yamaguchi et al. | |
| 2011/0009535 A1 | 1/2011 | Mikumo et al. | |

FOREIGN PATENT DOCUMENTS

| | | |
|---|---|---|
| JP | H08320314 A | 12/1996 |
| JP | 2004-513667 A | 5/2004 |
| JP | 2006-280933 A | 10/2006 |
| JP | 2007-040785 A | 2/2007 |
| JP | 2009-213609 A | 9/2009 |
| JP | 2011-081007 A | 4/2011 |

OTHER PUBLICATIONS

International Search Report of PCT/JP2013/055122, mailed May 28, 2013.

* cited by examiner

*Primary Examiner* — Christine T Mui
(74) *Attorney, Agent, or Firm* — Collard & Roe, P.C.

(57) ABSTRACT

An indicator for detecting peroxide can detect the peroxide through change of hue thereof by reacting the peroxide according to a predefined concentration and a predefined sterilization treatment condition thereof. The indicator has better resistance against weather or light and preservation stability than those of prior indicators including inorganic compounds or organic compounds as discoloration components, can clearly change an arbitrary hue thereof under suitable discoloration rate, and has visible distinguishability. The indicator for detecting peroxide includes powdery metal sulfide, that undergoes discoloration by reacting with the peroxide. In particular a discoloration layer including the metal sulfide is applied onto at least a portion of a base substrate.

10 Claims, 1 Drawing Sheet

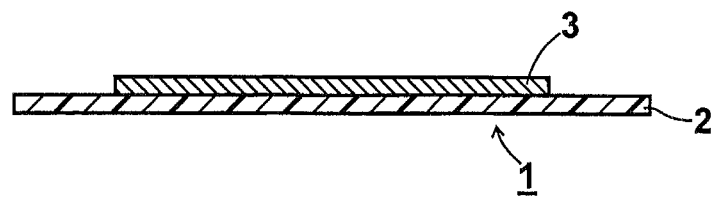

PEROXIDE INDICATOR

CROSS REFERENCE TO RELATED APPLICATIONS

This application is the National Stage of PCT/JP2013/055122 filed on Feb. 27, 2013, which claims priority under 35 U.S.C. §119 of Japanese Application No. 2012-043794 filed on Feb. 29, 2012, the disclosures of which are incorporated by reference. The international application under PCT article 21(2) was not published in English.

TECHNICAL FIELD

The present invention relates to an indicator used for detecting peroxides such as hydrogen peroxide, ozone and peracetic acid, in particular gaseous peroxides, for detecting whether a chemical sterilization treatment by peroxide, a chemical pasteurization treatment or a disinfectant treatment was carried out or not for confirmation thereof, or for detecting whether thus sterilization treatment, thus pasteurization treatment or thus disinfectant treatment was completed or not for confirmation thereof.

BACKGROUND OF THE ART

A sterilization treatment using peroxide as a pasteurization agent or a sterilization agent illustrated with ozone, hydrogen peroxide and peracetic acid has been carried out in a food field or a medical field in which harmless and clean production circumstances and hygiene managements are required. As thus chemical sterilization treatment methods, it is known to carried out a low-temperature sterilization method such as a gaseous sterilization method using a gas illustrated with an ozone gas and an ethylene oxide gas having a sterilizing activity, or a low-temperature plasma sterilization method using a sterilization activity by low-temperature plasma which is prepared through plasma activation of a gas illustrated with a hydrogen peroxide gas having an oxidizing activity. The low-temperature sterilization methods are capable of going through sterilization at low-temperature in a short time as compared to a high-temperature steam sterilization method using a high temperature and pressure aqueous vapor in an autoclave. The low-temperature sterilization methods are useful for sterilizing plastic products for which an autoclave is unable to be used. Therefore the low-temperature sterilization methods have been prevalent.

A discoloration indicators are used for indicating or affirming through change of hue whether the sterilization treatment were completed or not, or were effectively carried out or not. The discoloration indicators are required to change color according to conditions such as concentration of a sterilization agent or a pasteurization agent, and duration time of exposure thereof during sterilization treatment procedures.

For example, Patent Document 1 discloses an indicator for plasma sterilization comprising an azo dye, a compound as an auxiliary color coupler having a mercapto group or a dithiocarbamyl group, and a resin as a binder. A polyphenol compound or an aromatic carboxylic acid for development by the auxiliary color coupler is added thereto to prevent decomposition or disappearing of the azo dye during the sterilization treatment or color deterioration under high humidity after the discoloration. It discloses an exemplified indicator which changes from red to blue.

Patent Document 2 discloses an indicator for oxidative sterilization which utilises producing a development compound through reacting a primary amine with an aldehyde to evaluate effectivity of an sterilization process. According to this indicator, after either one of the primary amine and an aldehyde is kept away a pasteurization agent from reacting each other and another one is kept to be encapsulated in an ampule, the ampule is fractured and then both of them are contact each other in conducting the sterilization treatment in order to color. An exposure amount of the pasteurization agent such as hydrogen peroxide, peracetic acid, ethylene oxide, ozone, chlorine dioxide and the like is estimated by intensity of coloring thereof.

Thus pasteurization agent or sterilization agent used for the sterilization treatment behaves to be a gaseous phase. They are so toxic that human may be damaged. Therefore it is required to monitor or detect the concentration of those gases. As an indicator for detecting the gas, Patent Document 3 discloses an indicator for detecting an oxidative gas comprising at least one selected from the group consisting of an azo dye, a methine dye, triarylmethane dye, a thiazine dye. The indicator may include a cationic surface-activating agent as an auxiliary color coupler, silica as an extender pigment and an anthraquinone dyestuff as a dye respectively.

And as an indicator having a discoloration rate according to concentration of a hydrogen peroxide gas, Patent Document 4 discloses an indicator for detecting a hydrogen peroxide gas comprising a styrene-acrylic resin and/or a styrene-maleic resin and a methine dye. The indicator may include a cationic surface-activating agent as an auxiliary color coupler, and silica as an extender pigment.

Various indicators, which are best suited to detecting those sterilization treatments or gases, has been sold. However, as of now there are few indicators which are satisfied with preservation stability and visible distinguishability due to using an organic compound as a discoloration component such as an organic dyestuff. The indicators including the organic pigment tend to cause color deterioration because the pigments such as the included dyestuff and the like are decomposed by light. Furthermore the indicators have poor visible distinguishability and are difficult to evaluate an intermediate discoloration point, because hue changes from a chromatic color to other chromatic color or changes between close color. Especially unfamiliar operators are hard to instantaneously estimate whether the hue changes completely or not.

PRIOR ART DOCUMENT

Patent Document

[Patent Document 1] Japanese Unexamined Patent Application Publication No. 2009-213609A
[Patent Document 2] Japanese Unexamined Patent Application Publication No. 2006-280933A
[Patent Document 3] Japanese Unexamined Patent Application Publication No. 2011-81007A
[Patent Document 4] Japanese Unexamined Patent Application Publication No. 2007-40785A

SUMMARY OF THE INVENTION

Problems to be Solved by the Invention

The present invention has been developed to solve the aforementioned problems. And an object of the present invention is to provide an indicator for detecting peroxide that can detect the peroxide through change of hue thereof by reacting the peroxide according to a predefined concentration and a predefined sterilization treatment condition thereof, has more excellent resistance against weather or light and preservation stability than those of prior indicator including inorganic compounds or organic compounds as discoloration components, can clearly change an arbitrary hue thereof under suitable discoloration rate, and has visible distinguishability.

Means to Solve the Problems

An indicator for detecting peroxide of the present invention, which was made to achieve the aforementioned objects, comprises: powdery metal sulfide that undergoes discoloration through reacting with the peroxide.

In the indicator for detecting peroxide, the metal sulfide is at least one selected form the group consisting of bismuth sulfide, antimony sulfide, tungsten sulfide, and cobalt sulfide.

In the indicator for detecting peroxide, the metal sulfide has a volume-average particle diameter ranging from 0.1 to 30 μm in a volume-basis distribution obtained by a laser diffraction/scattering method.

In the indicator for detecting peroxide, the peroxide is ozone, hydrogen peroxide, or peracid.

The indicator for detecting peroxide, further comprises an invariable chromatic dye which is made to be invisible by the metal sulfide and makes hue of the dye appear through the discoloration.

In the indicator for detecting peroxide, a discoloration layer including the metal sulfide is applied onto at least a portion of a base substrate.

In the indicator for detecting peroxide, the base substrate is synthetic paper or plastic film.

In the indicator for detecting peroxide, the metal sulfide is packed in a breathable packaging.

The indicator for detecting peroxide, further comprises an iron compound with the metal sulfide.

In the indicator for detecting peroxide, the iron compound is iron(III) sulfate and/or iron halogenide.

Effect of the Invention

The indicator for detecting peroxide of the present invention can indicate discoloration of hue thereof through reacting with the peroxide such as hydrogen peroxide, ozone and peracetic acid, in particular gaseous peroxides. Therefore the indicator can detect those compounds. In this regard, a metal sulfide included as a discoloration component changes from grayish black to white or chromatic color such as pink. Since this discoloration of the hue is occurred in thus hue, the indicator for detecting peroxide has excellent clarity and visible distinguishability. Alternatively, other indicator may include an additional invariable chromatic dye whose hue differs from one of the metal sulfide. Therefore the hue of the indicator can change from achromatic color to chromatic color instead of achromatic discoloration from grayish black to white. In this matter, the hue of indicator after discoloration may be arbitrarily set up according to intended purposes or usage environments.

The indicator may be used for detecting confirmation of availability of a sterilization treatment or completion of the sterilization treatment using a sterilization agent or a pasteurization agent of peroxides as a subject being detected as well as detecting a peroxide gas. As regards the indicator for detecting peroxide, its hue of discoloration can be adjusted under an arbitrary discoloration rate according to the intended purposes or the usage environments. Therefore the indicator can confirm the availability of the sterilization treatment by exposing a given amount of the peroxide under a predetermined condition to achieve the discoloration.

The indicator for detecting peroxide of the present invention has following more excellent properties as compared to a prior indicator including inorganic compounds or organic compounds as discoloration components. The indicator has more superior resistance against weather or light and more excellent preservation stability, does not cause color deterioration even by environment influence such as exposing high-temperature and humidity or light of sunlight and so on under each stage of before/in/after use, and can maintain its hue thereby.

BRIEF DESCRIPTION OF THE DRAWINGS

FIG. 1 is a schematic cross-sectional view showing an indicator for detecting peroxide of the present invention.

MODE FOR CARRYING OUT THE INVENTION

Embodiments for which the present invention is applied will be described below in detail, but the scope of the present invention should not be limited to these embodiments.

An indicator for detecting peroxide of the present invention comprises powdery or granular metal sulfide preliminarily-pulverized as a discoloration component, and can indicate discoloration of its hue through reacting the discoloration component with gaseous peroxide of a subject being detected. By the discoloration of the hue, the indicator can confirm existence or non-existence of the subject being detected, or the availability of the sterilization treatment using a sterilization agent or a pasteurization agent of peroxides as the subject being detected.

An embodiment of the indicator for detecting peroxide will be precisely explained while referring to FIG. 1.

The indicator 1 for detecting peroxide composes a discoloration layer 3 including metal sulfide as a discoloration component on at least a part of base substrate 2. The discoloration layer 3 can indicate discoloration of its hue trough reacting with the peroxide.

The powdery metal sulfide included in the discoloration layer 3 is the discoloration component which originally shows grayish black, while its hue changes to other hue different from the grayish black, for example achromatic color such as white, or chromatic color such as pink and pale blue. The metal sulfide includes bismuth sulfide, antimony sulfide, tungsten sulfide and cobalt sulfide, all of which has excellent resistance against light.

The metal sulfide is preliminarily-pulverized by using a pulverizer to gain particles having the bare dispersion so as to be powdery or granular. The particle diameter thereof is regulated as weight-average particle diameter or volume-average particle diameter, and a discoloration rate is arbitrarily achieved thereby. The volume-average particle diameter of the metal sulfide is preferably ranges from 0.1 μm to 30 μm based on the volume-basis distribution by the laser diffraction scattering measurement method. It is more preferably to be 0.5 μm to 20 μm, furthermore preferably to be 0.5 μm to 13 μm (with the proviso that it is more preferably to be up to 12 μm, furthermore preferably to be up to 11 μm), still more preferably to be 1 μm to 11 μm, still furthermore preferably to be 1 μm to 10 μm. When the particle diameter of the metal sulfide becomes larger and rougher, the discoloration rate can become slower. And when the particle diameter of metal sulfide becomes smaller and finer, the discoloration rate can become faster.

The base substrate 2, on which the discoloration layer 3 is provided, is made of a piece of synthetic paper or plastic film whose shape is sheet-like, card-like, label-like, film-like shape and so on. Examples of the plastic film are a polyethylene terephthalate (PET) film and a polyethylene (PE) film.

Examples of the peroxide as the subject being detected are ozone, hydrogen peroxide, peracid specifically peracetic acid which generate hydrogen peroxide. Those peroxides may be an oxidative gas or a plasma-treated gas thereof, and can be exemplified with an ozone gas, a hydrogen peroxide gas, a peracetic acid gas, or a plasma-treated gas thereof.

The indicator 1 for detecting peroxide is prepared by the following procedures.

The metal sulfide is pulverized by using a pulverizer until its particle gets predetermined size, to become the discoloration component. If necessary, the metal sulfide may be pulverized with additional medium such as aliphatic hydrocarbon and aromatic hydrocarbon. After adding resin to the pulverized powdery metal sulfide, they are further pulverized. If necessary, vehicle is added thereto for adjusting appropriate viscosity. And they are mixed to prepare an ink. The ink is printed out on at least a part of base substrate 2 having a film-like shape, and then dried to form the discoloration layer 3. Accordingly the film-like indicator 1 for detecting peroxide is obtained.

A content of the metal sulfide of the discoloration component included in the discoloration layer 3 ranges preferably 1-30 weight %, more preferably 3-20 weight %.

A content of the resin included with the discoloration component ranges preferably 20-70 weight %, more preferably 30-50 weight %.

A content of the vehicle for mixing the discoloration component and the resin ranges preferably 5-40 weight %, more preferably 10-30 weight %.

The resin is not limited in so far as the discoloration property of the indicator is not impaired thereby and the adhesive property towards a subject being printed is sufficient. Examples of the resin are ethyl cellulose, nitrocellulose, butyral resin, acrylic resin such as acrylate resin or methacrylate resin, polyamide resin, phenol resin, rosin-modified maleic acid resin and so on. The resins may contain solvents. The resins may be a commercially available vehicle for an ink, for example a medium.

Examples of the solvent are xylene, ethylene glycol monobutyl ether, mineral spirit, and toluene.

The pulverizer is not limited in so far as metal sulfide is pulverized to have a desired particle diameter. Examples of the pulverizer are a ball mill, a mortar and a wonder blender (i.e. small-sized grinder mill).

Examples of a method for printing onto the base substrate 2 are a screen printing method, and an applying method using a brush. The thickness of the printed discoloration layer 3 is preferably 5-25 µm.

The obtained indicator 1 for detecting peroxide is used under a condition of existence of the peroxide of the subject being detected. When bismuth sulfide is used as the discoloration component in this case, the discoloration layer 3 responds. The hue of the grayish black of the discoloration layer 3, which is an original hue of bismuth sulfide as the discoloration component, changes to white so as to achieve the discoloration thereof. The discoloration component makes the discoloration of the hue change from grayish black to white. When an invariable chromatic dye is included with the discoloration component in the layer, the layer makes its changed hue adjust arbitrarily. For example, the invariable chromatic dye, whose chromatic hue differs from both hues before/after the discoloration of the metal sulfide, is included in the layer. In this case, it displays grayish black of original hue of the metal sulfide because the hue of the invariable chromatic dye is shielded by the metal sulfide before the discoloration. However, after the discoloration, it displays the hue of the invariable chromatic dye because the metal sulfide reacts with the peroxide as the subject being detected to get discolored into white and then the shielded hue of the invariable chromatic dye is appeared. Thus, when the invariable chromatic dye is included therein, it is possible to indicate the discoloration from achromatic color to chromatic color.

Besides, when cobalt sulfide is used as the discoloration component, the discoloration layer 3 responds. The hue of the grayish black of the discoloration layer 3, which is an original hue of cobalt sulfide as the discoloration component, changes to pink so as to achieve the discoloration thereof. As well as above-mentioned, when the invariable chromatic dye is included therein, it is possible to highlight the color difference of the discoloration or to indicate the discoloration arbitrarily.

Examples of the invariable chromatic dye are C.I. pigment red 170, and C.I. pigment violet 23. The content of the invariable chromatic dye preferably is 0.01-0.5 weight %, more preferably is 0.1-0.2 weight %.

The indicator for detecting peroxide may further comprise an iron compound with the metal sulfide as the discoloration component. The iron compound can accelerate a reaction rate between the peroxide as the subject being detected and the metal sulfide, and can adjust a discoloration rate of changing the hue according to purposes or conditions. Examples of the iron compound are iron halogenide such as iron(III) chloride, iron(II) bromide, and iron(II) iodide; iron sulfate such as iron(III) sulfate, and iron(II) sulfate. Among them, iron(III) sulfate or iron halogenide is more preferable. Thus iron compounds may be used solely or used to be mixed plurally. The content of the iron compound is preferably 0.1-10 weight %.

The indicator for detecting peroxide of the present invention is not limited to the exemplified indicator 1 for detecting peroxide, which comprises the base substrate 2 and the discoloration layer 3. The indicator, which is used as a spray or paint, may be in the form of a liquid. Also the indicator may be in the form of powder, which is packed in a breathable packaging made from polypropylene to be used.

EMBODIMENTS

Embodiments of the present invention will be precisely explained hereinafter, but the scope of the present invention is not limited to these examples.

Example 1

2 g of bismuth sulfide which is available from Wako Pure Chemical Industries, Ltd. was pulverized in a ball mill pot having a 100 mm diameter for three days and nights. After that, 10 g of medium, which is commercially available and includes 20-40 weight % of an acrylic resin as a resin, 25-35 weight % of ethylene glycol mono-normal-butyl ether and 15-25 weight % of mixture of aromatic hydrocarbons (i.e. petroleum naphtha) as vehicles, was added therewith in the ball mill pot, and then they were pulverized for further two days and nights. Xylene as a solvent medium which is available from Iwai Chemicals Company Ltd. was adequately added thereto for adjusting appropriate viscosity for the screen-painting to obtain an ink 1. The obtained ink 1 was respectively screen-printed under condition of 180 mesh onto various base substrates such as a PET film: LUMIRROR E20 (75 µm) which is available from Toray Industries, Inc., a PE film: Crisper K2323 (75 µm) which is available from Toyobo Co., Ltd., a polypropylene(PP)-type synthetic paper: YUPO-COAT VIS for printing (90 µm) which is available from YUPO Corporation, a synthetic paper: OPER MMW130 (75 µm) which is available from Nippon Paper Papylia Co., Ltd. After they were left into a room for one day and night to be dried, an indicator for detecting peroxide was prepared.

Incidentally, a volume-average particle diameter of the pulverized bismuth sulfide was 8.0 µm, when measuring through a laser diffraction/scattering method by using a laser diffraction particle diameter distribution analyzer: SALD-3100-WJA1:V1.00 which is available from Shimadzu Corporation.

Example 2

2 g of bismuth sulfide which is available from Wako Pure Chemical Industries, Ltd. was pound in a mortar having a 100 mm diameter for 15 minutes. 10 g of medium, which is commercially available and includes 20-40 weight % of an acrylic resin as a resin, 25-35 weight % of ethylene glycol mono-normal-butyl ether and 15-25 weight % of mixture of aromatic hydrocarbons (i.e. petroleum naphtha) as vehicles, was added therewith in a ball mill pot, and then they were pulverized for further 10 minutes. Xylene as a solvent medium which is available from Iwai Chemicals Company Ltd. was adequately added thereto for adjusting appropriate viscosity for the screen-painting to prepare an ink 2. The obtained ink 2 was respectively screen-printed under condition of 180 mesh onto various base substrates as similar as Example 1. After they were left into a room for one day and night to dried, an indicator for detecting peroxide were prepared.

Incidentally, a volume-average particle diameter of the pulverized bismuth sulfide was 9.6 µm, when measuring through the method and the procedures as similar as Example 1.

Example 3

An ink 3 was prepared under the conditions and procedures as similar as Example 1 except for 30 g of Xylene was added to bismuth sulfide, and an indicator for detecting peroxide were prepared by using the ink.

Incidentally, a volume-average particle diameter of the pulverized bismuth sulfide was 2.6 µm, when measuring through the method and the procedures as similar as Example 1.

(Evaluation of Indicator for Detecting Peroxide)

After each of the indicators for detecting peroxide prepared in Examples 1-3 was exposed to an atmosphere above a solution including 34.5 weight % (wt %) of hydrogen peroxide at 50° C. for 2 hours, an appearance of its discoloration thereof was observed. Results of the discoloration according to an exposure time to a hydrogen peroxide gas are respectively shown in Table 1 in a case using the indicator for detecting peroxide prepared in Example 1, in Table 2 in a case using the indicator for detecting peroxide prepared in Example 2, and in Table 3 in a case using the indicator for detecting peroxide prepared in Example 3.

TABLE 1

| Species of Base Substrate | | Exposure Time | | | | |
|---|---|---|---|---|---|---|
| | | 0 hour | 1 hour | 2 hours | 3 hours | 4 hours |
| Example 1 | PET Film | Grayish Black | Gray | White | White | White |
| | PE Film | Grayish | Gray | White | White | White |

TABLE 1-continued

| Species of Base Substrate | | Exposure Time | | | | |
|---|---|---|---|---|---|---|
| | | 0 hour | 1 hour | 2 hours | 3 hours | 4 hours |
| | PP-type Synthetic Paper | Black Grayish Black | Gray | White | White | White |
| | Synthetic Paper | Grayish Black | Gray | White | White | White |

TABLE 2

| Species of Base Substrate | | Exposure Time | | | | |
|---|---|---|---|---|---|---|
| | | 0 hour | 1 hour | 2 hours | 3 hours | 4 hours |
| Example 2 | PET Film | Grayish Black | Grayish Black | Gray | Gray | White |
| | PE Film | Grayish Black | Grayish Black | Gray | Gray | White |
| | PP-type Synthetic Paper | Grayish Black | Grayish Black | Gray | Gray | White |
| | Synthetic Paper | Grayish Black | Grayish Black | Gray | Gray | White |

TABLE 3

| Species of Base Substrate | | Exposure Time | | | | |
|---|---|---|---|---|---|---|
| | | 0 hour | 1 hour | 2 hours | 3 hours | 4 hours |
| Example 3 | PET Film | Grayish Black | White | White | White | White |
| | PE Film | Grayish Black | White | White | White | White |
| | PP-type Synthetic Paper | Grayish Black | White | White | White | White |
| | Synthetic Paper | Grayish Black | White | White | White | White |

As shown in Tables 1-3, it is evident that the smaller the particle diameter of bismuth sulfide became, the faster the discoloration rate of the discoloration reaction became. And the indicator of Example 3, whose bismuth sulfide was pulverized under a wet condition and had a fine particle diameter, even changed its hue to gray within only 0.5 hour of the exposure time to a hydrogen peroxide gas, as compared with the one of Example 3, whose bismuth sulfide was pulverized under a dry condition.

As shown in Tables 1-2, it is evident that difference of the particle diameter of the bismuth sulfide as the discoloration component contributed the discoloration rate. Especially it is evident that the indicator for detecting peroxide which included bismuth sulfide having the finer particle diameter got the faster discoloration rate as compared with the one including bismuth sulfide having the larger particle diameter.

After the indicators for detecting peroxide prepared in Examples 1 and 2 were respectively encapsulated into a sterilization bag for STERRAD: RollR which is available from Johnson & Johnson K.K., they were placed in a plastic container. They were inserted into a hydrogen peroxide gas sterilization chamber which sterilizes them by the generated hydrogen peroxide. After a sterilization treatment was conducted under sterilization conditions where pulse times was 4, pulse pressure was from 0.4 to 500 Torr, and temperature was 50° C., an appearance of its discoloration thereof was respectively observed.

Results of both hues of the discoloration on the indicator for detecting peroxide obtained in Examples 1 and 2 before/after the pasteurization treatment by using the hydrogen peroxide gas sterilization chamber, is shown in the following Table 4.

TABLE 4

|  | Species of Base Substrate | Before Sterilization Treatment | After Sterilization Treatment |
| --- | --- | --- | --- |
| Example 1 (Pulverized in Ball Mill) | PET film | Grayish Black | White |
| Example 1 (Pound in Mortar) | PET film | Grayish Black | Gray |

(Verification Test of Resistance Against Light and Weather)

As for the verification test of the resistance against the light, the indicators for detecting peroxide prepared in Example 1, which were respectively in states before/after the discoloration, were exposed to the sunlight for 1 month. A case, where it did not cause color deterioration under exposure of the sunlight for 1 month, was assumed as "Excellent". A case, where it causes a little color deterioration under exposure of the sunlight for 1 month, was assumed as "Good". A case, where it causes absolute color deterioration under exposure of the sunlight for 1 month, was assumed as "Poor". The results thereof are shown in Table 5. As for resistance against weather, the other indicators, which were respectively in states before/after the discoloration, were placed under circumstance of 40° C.-80% Rh in a thermo-hygrostat LH43-12P which is available from Nagano Science Co., Ltd. Then the appearance of the indicators for detecting peroxide was observed. Incidentally, for a comparative example, a commercially available indicator, which includes an organic dyestuff as a discoloration component and changes from yellow to red by hydrogen peroxide, were verified as well as above-mentioned test. The results are shown in Table 5 together.

TABLE 5

| from Hue before Discoloration to Hue after Discoloration | | Example 1 from Grayish Black to White | Comparative Example from Red to Yellow |
| --- | --- | --- | --- |
| Resistance against Light | before Discoloration | Excellent | Poor |
|  | After Discoloration | Excellent | Poor |
| Resistance against Weather | before Discoloration | Excellent | Good |
|  | After Discoloration | Excellent | Good |

As shown in Table 5, it is evident that the indicator having the inorganic compound as the discoloration component of Example 1 indicated more excellent of the resistance against the light and the weather than one having the organic compound as the discoloration component of Comparative Example.

Example 4

2 g of bismuth sulfide which is available from Wako Pure Chemical Industries, Ltd. and 0.02 g of Seikafast Red 1537-B (i.e. C.I. Pigment Red 170) which is available from Dainichiseika Color & Chemical Mfg. Co., Ltd. were pulverized in a ball mill pot having a 100 mm diameter for three days and nights. After that, 10 g of medium, which is commercially available and includes 20-40 weight % of an acrylic resin as a resin, 25-35 weight % of ethylene glycol mono-normal-butyl ether and 15-25 weight % of mixture of aromatic hydrocarbons (i.e. petroleum naphtha) as vehicles, was added therewith in the ball mill pot, and then they were pulverized for further two days and nights. Xylene as a solvent medium which is available from Iwai Chemicals Company Ltd. was adequately added thereto for adjusting appropriate viscosity for the screen-painting to obtain an ink 4. The obtained ink 4 was respectively screen-printed under condition of 180 mesh onto various base substrates such as a PET film. LUMIRROR E20 (75 μm) which is available from Toray Industries, Inc., a PE film: Crisper K2323 (75 μm) which is available from Toyobo Co., Ltd., a polypropylene(PP)-type synthetic paper: YUPOCOAT VIS for printing (90 μm) which is available from YUPO Corporation, a synthetic paper: OPER MMW130 (75 μm) which is available from Nippon Paper Papylia Co., Ltd. After they were left into a room for one day and night to dried, an indicator for detecting peroxide was prepared.

Example 5

Seikafast Red 1537-B (i.e. C.I. Pigment Red 170) which is available from Dainichiseika Color & Chemical Mfg. Co., Ltd. in Example 4 was shifted to FASR VIOLET 2321 D (i.e. C.I. Pigment Violet 23) which is available from SANYO COLOR WORKS LTD., a indicator for detecting peroxide was prepared as well as Example 4.

(Evaluation of Indicator for Detecting Peroxide)

After each of the indicators for detecting peroxide prepared in Examples 4-5 was exposed to an atmosphere above a solution including 34.5 weight % (wt %) of hydrogen peroxide at 50° C. for 2 hours, an appearance of its discoloration thereof was observed. Results of the discoloration according to exposure to a hydrogen peroxide gas are shown in Table 6.

TABLE 6

|  | Before Sterilization Treatment | After Sterilization Treatment |
| --- | --- | --- |
| Example 4 | Grayish Black | Red |
| Example 5 | Grayish Black | Blue |

Verification Test of Effect of Iron Compound Against Discoloration Rate

Example 6

2 g of bismuth sulfide which is available from Wako Pure Chemical Industries, Ltd. was pulverized in a ball mill pot having a 100 mm diameter for three days and nights. After that, 10 g of medium, which is commercially available and includes 20-40 weight % of an acrylic resin as a resin, 25-35 weight % of ethylene glycol mono-normal-butyl ether and 15-25 weight % of mixture of aromatic hydrocarbons (i.e. petroleum naphtha) as vehicles, was added therewith in the ball mill pot, and then they were pulverized for further two days and nights. Xylene as a solvent medium which is available from Iwai Chemicals Company Ltd. was adequately added thereto for adjusting appropriate viscosity for the screen-painting to obtain an ink 1. 5 g of the obtained ink 1 was divided up. 0.1-0.2 g of various iron compounds was respectively added thereto, and they were kneaded in a mortar having 100 mm of diameter for 15 minutes. Then they were respectively screen-printed under condition of 180 mesh onto a polypropylene (PP) type synthetic paper: CAERE (80 μm) which is available from Nakamoto Packs Co., Ltd. After they were left into a room for one day and night to dried, an indicator for detecting peroxide was prepared.

(Evaluation of Indicator for Detecting Peroxide)

After each of the indicators for detecting peroxide prepared in Example 6 was exposed to an atmosphere above a solution including 34.5 weight % (wt %) of hydrogen peroxide at 50° C. for 1 hour, an appearance of its discoloration thereof was observed. Results of the discoloration according to an exposure time to a hydrogen peroxide gas are respectively shown in Table 7.

TABLE 7

| | | Exposure Time | | | | |
|---|---|---|---|---|---|---|
| | Additives | 0 min. | 15 min. | 30 min. | 45 min. | 60 min. |
| Example 6 | Non | Grayish Black | Grayish Black | Gray | Pale Gray | White |
| | Iron(III) Chloride | Grayish Black | Brownish Yellow | Pale Yellow | Pale Yellow | Pale Yellow |
| | Iron(II) Bromide | Grayish Black | Grayish Black | Gray | Pale Yellow | Pale Yellow |
| | Iron (II) Iodide | Grayish Brown | Brownish Yellow | Pale Brownish Yellow | Pale Brownish Yellow | Pale Brownish Yellow |
| | Iron(III) Sulfate | Grayish Black | Pale Gray | White | White | White |
| | Iron(II) Sulfate | Grayish Black | Grayish Black | Gray | Pale Gray | White |

As shown in Table 7, it is evident that the sample indicator made from the ink composition adding the iron compound, in particular the iron(III) sulfate or the iron halogenide, achieved the discoloration in shorter time and provided the faster discoloration rate than them of the sample indicator using no iron compound. In this manner, it is obvious that the indicator gets effects in acceleration of the rate of the discoloration reaction when it includes the iron compound.

INDUSTRIAL APPLICABILITY

The indicator for detecting peroxide of the present invention can be used as an indicator to detect an oxidative gas such as hydrogen peroxide gas or peracetic acid gas, or can be used as another indicator to detect of availability of the sterilization treatment such as the ozone sterilization treatment, hydrogen peroxide low-temperature plasma sterilization and hydrogen peroxide gas treatment.

EXPLANATION OF LETTERS OR NUMERALS

1: indicator for detecting peroxide, 2: base substrate, 3: discoloration layer

What is claimed is:

1. An indicator for detecting peroxide comprising:
   a grayish black discoloration component comprising a powdery metal sulfide of 1-30 weight % that undergoes discoloration to an achromatic color or a chromatic color having a hue different from grayish black through reacting with the peroxide.

2. The indicator for detecting peroxide according to claim 1, wherein the metal sulfide is at least one selected from the group consisting of bismuth sulfide, antimony sulfide, tungsten sulfide, and cobalt sulfide.

3. The indicator for detecting peroxide according to claim 1, wherein the metal sulfide has a volume-average particle diameter ranging from 0.1 to 30 μm in a volume-basis distribution obtained by a laser diffraction/scattering method.

4. The indicator for detecting peroxide according to claim 1, wherein the peroxide is ozone, hydrogen peroxide, or peracid.

5. The indicator for detecting peroxide according to claim 1, further comprising an invariable chromatic dye which is made to be invisible by the metal sulfide and makes hue of the dye appear through the discoloration.

6. The indicator for detecting peroxide according to claim 1, wherein the discoloration component comprises a discoloration layer including the metal sulfide applied onto at least a portion of a base substrate.

7. The indicator for detecting peroxide according to claim 6, wherein the base substrate is synthetic paper or plastic film.

8. The indicator for detecting peroxide according to claim 1, wherein the metal sulfide is packed in a breathable packaging.

9. The indicator for detecting peroxide according to claim 1, further comprising an iron compound with the metal sulfide.

10. The indicator for detecting peroxide according to claim 9, wherein the iron compound is iron(III) sulfate and/or iron halogenide.

* * * * *